United States Patent [19]

Flemer, III

[11] Patent Number: Plant 7,731

[45] Date of Patent: Dec. 3, 1991

[54] ROBINIA 'PURPLE CROWN'

[75] Inventor: William Flemer, III, Princeton, N.J.

[73] Assignee: Rutgers University, New Brunswick, N.J.

[21] Appl. No.: 520,358

[22] Filed: May 7, 1990

[51] Int. Cl.[5] ..... A01H 5/00

[52] U.S. Cl. ..... Plt./51

[58] Field of Search ..... Plt./51, 52

*Primary Examiner*—Howard J. Locker

*Attorney, Agent, or Firm*—Frank B. Robb

[57] ABSTRACT

A seedling discovered growing in a cultivated area in a row of seedlings resulting from a cross between *Robinia hispida,* and *Robinia pseudoacacia,* and noticed because of its more vigorous, narrow upright crown of branches, and particularly at the time of blooming for its abundant purple pea-shaped flowers.

2 Drawing Sheets

BACKGROUND OF THE DISCLOSURE

As a hybridizer, and grower of many different plants during the operation of a commercial nursery, I have been particularly careful to observe various decorative plants and particularly trees which I feel have decided commercial appeal.

As this suggests, when I find new varieties of plants each of which have some attraction which I deem outstanding, or which suggest that improvement of each may result from crossing them, I have caused that to be done, usually resulting in a new cultivar which is commercially appealing.

This naturally results because of improved characteristics where I have had an opportunity to observe the parent plants and have reason to believe a cross would result in a plant which my nursery would grow and sell to others.

SPECIFIC DESCRIPTION OF THE DISCLOSURE

This particular invention relates to a new hybrid of Robinia, which was discovered as a seedling in a row of seedlings of *Robinia hispida,* being a cross with *Robinia pseudoacacia.*

Continued observation over time disclosed that the seedling was more vigorous growing with a narrow and upright crown of branches. Later when the seedling came into bloom it proved to be abundant flowering, bearing thousands of pendulous racemes of purple pea-shaped flowers having a mild fragrance.

As is customary in the nursery in which I carry on breeding and development of flowering trees and other decorative plants, I have caused my new hybrid which I have chosen to call 'Purple Crown', to be asexually propagated by grafting on bare root understocks, observing that the same comes true in successive generations and is in my judgment an attractive, decorative plant for many different types of display.

In continuing observation of successive generations of this new hybrid, I note that it is almost thornless on mature branches.

As to its form, my new hybrid may be described as intermediate between the parent species.

When compared with *R. hispida,* which is a spreading shrub about 1.5 m. tall with bristley twigs and *R. pseudoacacia* which is a tall and narrow tree up to 20 m. tall with thorny twigs, my hybrid is intermediate.

During a long period of growth and observation of my new plant, I have noted that it is tolerant of hot and dry weather and also of soils having high pH. content.

In observing the growth rate of my new hybrid and using a one year term as a basis, I have found that the average height at the end of the first summer's growth is between 1.5 and 2.0 meters.

Sister seedlings over the same time period attain average height of 1.3 to 1.6 meters.

*Robinia pseudoacacia* may be expected to reach heights of 2.3 to 2.6 meters in that time.

By comparison *Robinia hispida* may average a height of 0.5 to 0.7 meters over the same time.

My new plant does not appear to be susceptible to diseases which may be peculiar to Robinia in general, and it has been found that in years with hot summers when *Robinia pseudoacacia* clones such as 'Frisia' (unpatented) and 'Umbra culifera' show marginal heat scorch on the leaflets, my new variety is unharmed.

My new variety has not exhibited leaf chlorosis in soils with a pH as high as 7.5.

Breeding and growing of my new variety have taken place in the vicinity of Plainsboro Township, Middlesex County, N.J.

Specific characteristics of my new hybrid are summarized in the following, and where reference to color is made the drawing discloses in FIG. 1, a view of a tree of my new hybrid.

FIG. 2 is a detailed view of my hybrid to show the shape and color of the flowers on one of the racenes.

The color notations are made from comparison with the Munsell Color Fan, noting that the colors are as nearly true as it is possible to make the same in photographs of which the figures are examples.

DETAILED DESCRIPTION OF THE INVENTION

Figure 1:
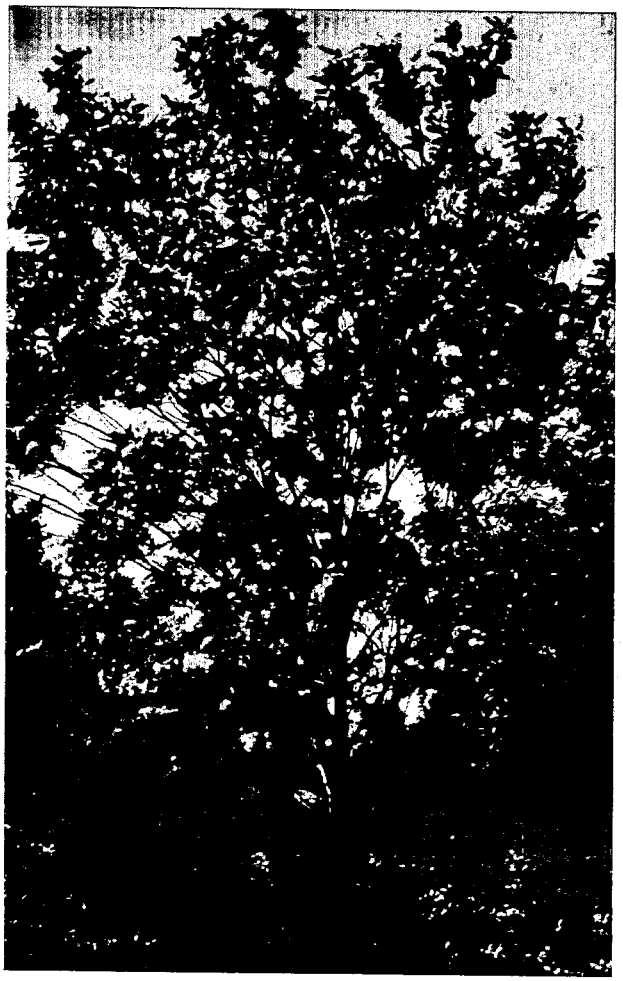
Figure 2:
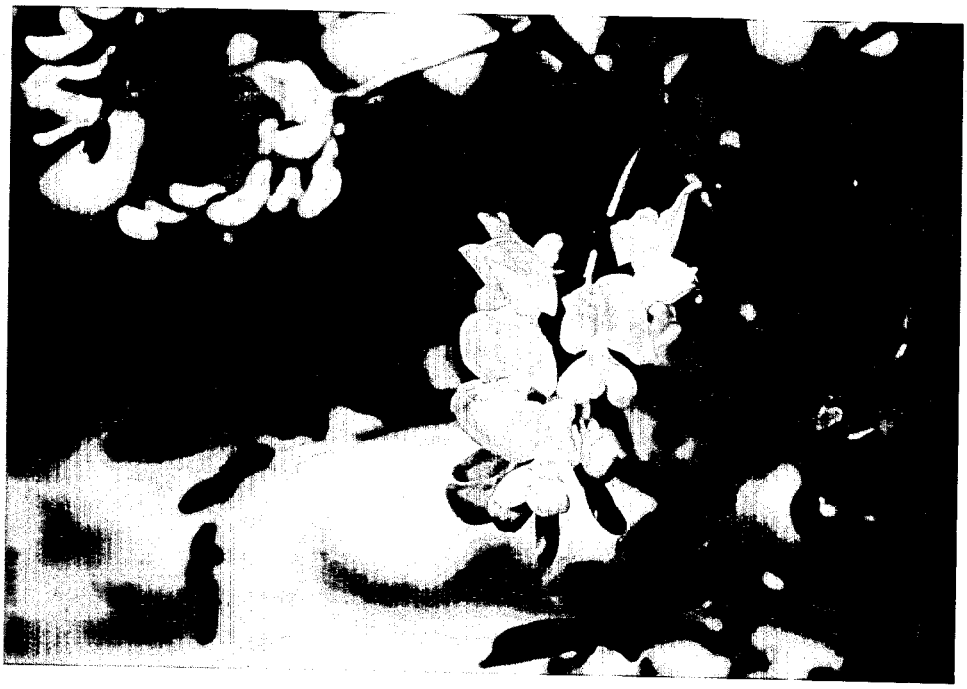

Parentage:

*Seed parent.—Robinia hispida.*

*Pollen parent.—Robinia pseudoacacia.*

Tree: Small; upright; dense and hardy.

*Trunk.*—Slender; rough.

*Branches.*—Slender; smooth with minute paired thorns beside the nodes. Color — Moderate brown, 5 YR 3/3. Lenticels — Moderately abundant, minute. Number — 15 to 17 per square cm. of twig surface.

*Leaves.*—Moderately abundant; compound; medium thickness. Length — 18 to 24 cm. Width — 12 to 13 cm. Shape — Compound; 12 to 14 leaflets, each leaflet 6 cm. long, 3.5 cm. wide. Color — Moderate olive green, 7.5 G.Y. 4/4. Margin — Smooth edge leaflets. Petiole — Short; 4 to 5 cm. long. Glands — None.

*Flower buds.*—Very hard; minute.

Flowers: Borne in pendulous racemes 15 to 18 flowers per raceme.

*First bloom.*—May 20.

*Full bloom.*—May 24.

*Quantity.*—Abundant; mildly fragrant.

*Size.*—Medium.

Petalage: Pea-shaped flowers, calyx campanulate, standard sub-orbicular and reflexed, keel incurved its petals united below.

*Shape of petals.*—Pea-shaped; 5 petals. Size — Length 2.1 cm. Width 2.5 cm.

*Color.*—Strong reddish purple 2.5 RP 5/10.

Fruits: Pods lightly hirsute, 4 to 6 cm. long, rarely borne, 1 to 3 seeds.

*Abundance.*—Very sparse.

*Size.*—Pods 4 to 6 cm. long.

*Color.*—Moderate brown.

I claim:

1. A new and distinct Robinia hybrid as described and illustrated characterized as to novelty by the vigorous growth, with narrow more upright crown of branches than either parent, the abundant flowering resulting in pendulous racemes of purple pea-shaped flowers with mild fragrance, nearly thornless when branches are mature, and its tolerance of heat, drought and high pH soils.

* * * * *